United States Patent
Combadiere et al.

(10) Patent No.: US 9,434,766 B2
(45) Date of Patent: Sep. 6, 2016

(54) CCR2 ANTAGONIST PEPTIDES

(75) Inventors: Christophe Combadiere, Magny le Hongre (FR); Florian Sennlaub, Paris (FR); Constance Auvynet, Paris (FR); Sylvian Chemtob, Cote St Luc (CA); Christiane Quiniou, Montreal (CA)

(73) Assignee: Universite Pierre Et Marie Curie (Paris 6), Paris (FR)

( * ) Notice: Subject to any disclaimer, the term of this patent is extended or adjusted under 35 U.S.C. 154(b) by 108 days.

(21) Appl. No.: 14/129,758

(22) PCT Filed: Jun. 26, 2012

(86) PCT No.: PCT/EP2012/062379
§ 371 (c)(1),
(2), (4) Date: Sep. 4, 2014

(87) PCT Pub. No.: WO2013/000922
PCT Pub. Date: Jan. 3, 2013

(65) Prior Publication Data
US 2015/0011477 A1 Jan. 8, 2015

(30) Foreign Application Priority Data

Jun. 27, 2011 (EP) .................................. 11305816

(51) Int. Cl.
*C07K 7/06* (2006.01)
*C07K 7/08* (2006.01)
*C07K 14/715* (2006.01)
*A61K 38/00* (2006.01)

(52) U.S. Cl.
CPC . *C07K 7/08* (2013.01); *C07K 7/06* (2013.01); *C07K 14/7158* (2013.01); *A61K 38/00* (2013.01)

(58) Field of Classification Search
None
See application file for complete search history.

(56) References Cited

U.S. PATENT DOCUMENTS

2005/0037430 A1 2/2005 Khan et al.
2009/0258436 A1* 10/2009 Hornbeck .............. C07K 16/18
436/501

FOREIGN PATENT DOCUMENTS

WO 9845322 A2 10/1998
WO 0131006 A2 5/2001
WO 2013000922 A1 1/2013

OTHER PUBLICATIONS

'T Hart et al., Modelling of multiple sclerosis: lessons learne in a non-human primate, Oct. 2004, The Lancet Neurology 3(10):588-597.*
Werkerle et al., Animal models of multiple sclerosis, 2006,Drug Discovery Today: Disease Models 3(4):359-367.*
Ransohoff, R. M., Animal models of multiple sclerosis: the good, the bad and the bottom line, Aug. 2012, Nature Neuroscience15(8):1074-1077.*
Behan et al., The sad plight of multiple sclerosis research (low on fact, high on fiction): critical data to support it being a neurocristopathy, 2010, Inflammopharmacology 18:265-290.*
Struthers et al., "CCR2 Antagonists," Current Topics in Medicinal Chemistry (2010); 10(13):1278-1298.
Xia et al., "Recent Developments in CCR2 Antagonists," Expert Opin. Ther. Patents (2009); 19(3):295-303.
Gong et al., "An Antagonist of Monocyte Chemoattractant Protein 1 (MCP-1) Inhibits Arthritis in the MRL-LPR Mouse Model," The Journal of Experimental Medicine (Jan. 1, 1997); 180(1):131-137.
McQuibban et al., "Matrix Metalloproteinase Processing of Monocyte Chemoattractant Proteins Generates CC Chemokine Receptor Antagonists with Anti-Inflammatory Properties in Vivo," Blood (Aug. 15, 2002); 100 (4):1160-1167.
Birren et al. Sequence of XM_001558132.1, Botryotinia fuckeliana B05.10 predicted protein, EMBL/GenBank/DDBJ database, Aug. 21, 2007.

* cited by examiner

*Primary Examiner* — John Ulm
(74) *Attorney, Agent, or Firm* — Fox Rothschild LLP; Jianming Jimmy Hao

(57) ABSTRACT

The invention relates to a peptide comprising the following amino acid sequence Thr-Phe-Leu-Lys (SEQ ID NO: 17) or Thr-Phe-Leu-Lys-Cys (SEQ ID NO: 1), useful as a CCR2 non-competitive antagonist peptide.

6 Claims, 9 Drawing Sheets

CCR2 ANTAGONIST PEPTIDES

Figures 1A, 1B:
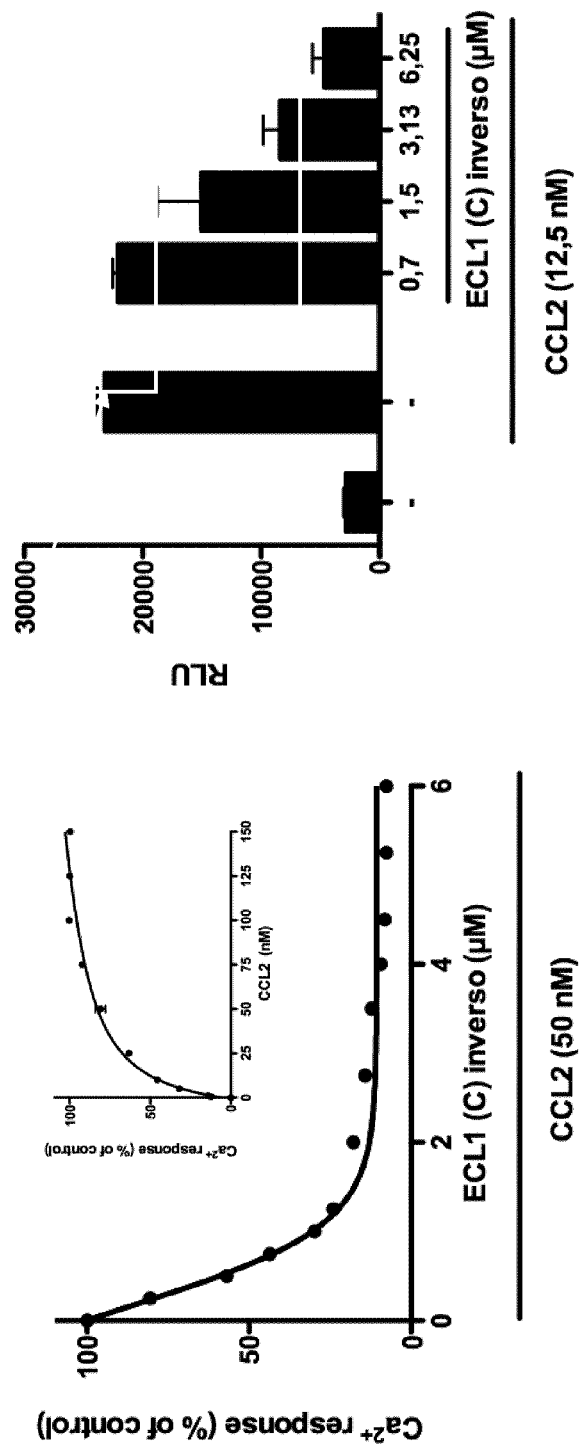

The present application is the U.S. National Phase of International Patent Application Serial No. PCT/EP2012/062379, filed Jun. 26, 2012, which claims the benefit of European Patent Application Serial No. 11305816.8, filed Jun. 27, 2011. The aforementioned applications are hereby incorporated by reference in their entireties.

The invention relates to CC chemokine receptor 2 (CCR2) antagonist peptides.

BACKGROUND OF THE INVENTION

CCR2 is a member of the GPCR (G-protein coupled receptor) family of receptors, as are all known chemokine receptors and are expressed by monocytes and memory T-lymphocytes. The CCR2 signaling cascade involves activation of heterotrimeric G proteins, phospholipases (and notably PLCβ2), protein kinases like PKC and PI-3K and cytosolic elevation of calcium.

Chemoattractant cytokines (i.e., chemokines) are relatively small proteins (8-10 kD) which trigger the migration of cells. The chemokine family is divided into four subfamilies based on the number and space of amino acid residues between the first and second highly-conserved cysteines.

The chemokine termed CCL2 (also known as Monocyte chemotactic protein-1 or MCP-1) is a member of the CC chemokine subfamily (wherein CC represents the subfamily having adjacent first and second cysteines) and binds to the cell-surface chemokine receptor 2 (CCR2). CCL2 is a potent chemotactic factor which, after binding to CCR2, mediates monocyte and lymphocyte migration (i.e., chemotaxis) toward a site of inflammation. CCL2 is produced by a wide variety of cell types in response to inflammatory conditions, such as cardiac muscle cells, blood vessel endothelial cells, fibroblasts, chondrocytes, smooth muscle cells, mesangial cells, alveolar cells, T-lymphocytes, macrophages, neurons and the like.

After monocytes enter the inflammatory tissue and differentiate into macrophages, monocyte differentiation provides a secondary source of several proinflammatory modulators, including tumor necrosis factor-alpha (TNFα) interleukin-1 (IL-1), CXCL-8 (a member of the CXC chemokine subfamily, wherein CXC represents one amino acid residue between the first and second cysteines), IL-12, arachidonic acid metabolites (e.g., $PGE_2$ and $LTB_4$), oxygen-derived free radicals, matrix metalloproteinases and complement components.

Animal model studies of chronic inflammatory diseases have demonstrated that inhibition of binding between CCL2 and CCR2 by an antagonist suppresses the inflammatory response. The interaction between CCL2 and CCR2 has been implicated (see Rollins B J, Monocyte chemoattractant protein 1: a potential regulator of monocyte recruitment in inflammatory disease, Mol. Med. Today, 1996, 2:198; and Dawson J, et al., Targeting monocyte chemoattractant protein-1 signaling in disease, Expert Opin. Ther. Targets, 2003 Feb. 7(1):35-48) in inflammatory disease pathologies such as uveitis, atherosclerosis, rheumatoid arthritis, multiple sclerosis, Crohn's Disease, nephritis, organ allograft rejection, fibroid lung, renal insufficiency, diabetes and diabetic complications, diabetic nephropathy, diabetic retinopathy, diabetic retinitis, diabetic microangiopathy, tuberculosis, sarcoidosis, invasive staphylococcia, inflammation after cataract surgery, allergic rhinitis, allergic conjunctivitis, chronic urticaria, allergic asthma, periodontal diseases, periodonitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

Monocyte migration is inhibited by CCL2 antagonists (either antibodies or soluble, inactive fragments of MCP-1) which have been shown to inhibit the development of arthritis, asthma, and uveitis. Both CCL2 and CCR2 knockout (KO) mice have demonstrated that monocyte infiltration into inflammatory lesions is significantly decreased. In addition, such KO mice are resistant to the development of experimental allergic encephalomyelitis (EAE, a model of human multiple sclerosis), cockroach allergen-induced asthma, atherosclerosis, and uveitis. Rheumatoid arthritis and Crohn's Disease patients have improved during treatment with TNF-α antagonists (e.g., monoclonal antibodies and soluble receptors) at dose levels correlated with decreases in CCL2 expression and the number of infiltrating macrophages.

Thus, CCR2 antagonists represent a new class of important therapeutic agents. So far efforts have focused on developing either chemicals (see e.g. Brodmerkel et al, J. Immunol, 2005, 175:5370-7378) or anti-CCR2 antibodies (see e.g. U.S. Pat. No. 7,566,539).

There remains a need for specific CCR2 antagonist small molecules for preventing, treating or ameliorating a CCR2 mediated disorder.

SUMMARY OF THE INVENTION

The inventors designed a series of small peptides between 5 and 7 amino acids from the extracellular juxtamembranous regions of CCR2. Among all the peptides tested, the heptapeptide LGTFLKC, named ECL1 (C) inverso, presented the most interesting properties as a CCR2 non competitive antagonist peptide. This peptide corresponds to an inverted sequence in the third transmembrane domain of CCR2, more precisely in the juxtamembranous and N-terminal region of the third transmembrane domain.

The invention thus provides a peptide comprising, or consisting of, the following amino acid sequence Thr-Phe-Leu-Lys-Cys (SEQ ID NO:1).

The inventors then realized that the Cysteine residue could be removed or replaced, while still showing an antagonist CCR2 activity of interest, in particular the corresponding peptides still exhibit the level of activity of peptide of SEQ ID NO:1.

The invention thus further provides a peptide comprising, or consisting of, the following amino acid sequence Thr-Phe-Leu-Lys (SEQ ID NO:17).

The invention further encompasses peptides comprising, or consisting of a sequence deriving from SEQ ID NO:1 or SEQ ID NO:17 by one or more chemical modifications that confer resistance to proteolysis, or a sequence deriving from SEQ ID NO:1 or SEQ ID NO:17 by one or more conservative substitutions.

Preferably all or part of the amino acids are in D configuration.

Another subject of the invention is a compound that comprises any one of said peptides linked to at least one non-peptide moiety that may be polyethylene glycol for instance.

A further subject of the invention is a pharmaceutical composition comprising a peptide or compound as herein described, in association with a pharmaceutically acceptable carrier.

The peptides of the invention are easy to produce, and to administer.

LEGENDS TO THE FIGURES

FIG. 1: ECL1 (C) inverso is a potent antagonist of CCR2. (A) Inhibitory effect of ECL1 (C) inverso at indicated concentrations on calcium release induced by CCL2 (50 nM) on HEK-CCR2. The $IC_{50}$ for ECL1 (C) inverso is 0.75 µM. One representative experiment of three is shown and data are fitted with a standard dose response curve (GraphPad Prism 5 software). Insert: HEK-CCR2 cells tested for calcium response to CCL2 at indicated concentrations enable to determine an $EC_{80}$ of 50 nM. (B) Inhibitory effect of ECL1 (C) inverso on β-arrestin recruitment induced by CCL2 at an $EC_{80}$ of 12.5 nM. Data represent triplicates from three independent experiments.

FIG. 2: ECL1 (C) inverso is an antagonist specific of CCR2. (A) No inhibitory effect of ECL1 (C) inverso at indicated concentrations on calcium release induced by CCL5 (25 nM) on HEK-CCR5 (●) or HEK-CCR1 (▲), by CX3CL1 (20 nM) on HEK-CX3CR1 (▼) or by ATP (10 µM) on HEK cells (□). (B) No cytotoxicity effect of ECL1 (C) inverso at indicated concentrations on HEK-CCR2 after 4 hours of incubation at 37° C., 5% $CO_2$. Triplicates were repeated three times independently.

Figure 3:
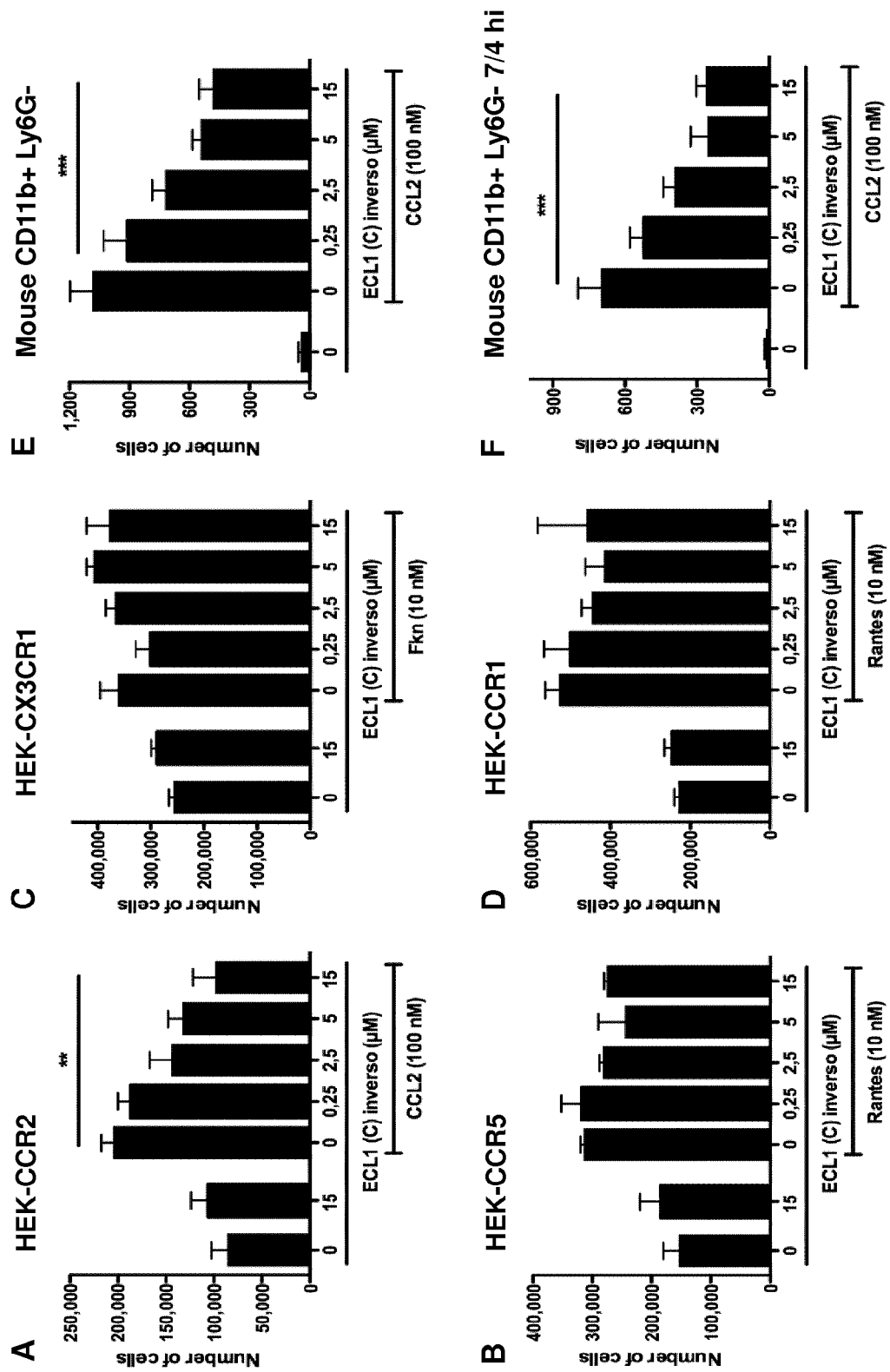

FIG. 3: ECL1 (C) inverso specifically inhibits the migration of HEK-CCR2 cells stimulated by CCL2. ECL1(C) inverso inhibits the migration of HEK-CCR2 induced by CCL2 at 100 nM (A) with an $IC_{50}$ of 2 µM, but not the one of HEK-CCR5 induced by CCL5 (10 nM) (B), of HEK-CX3CR1 induced by CX3CL1 (10 nM) (C) or of HEK-CCR1 induced by CCL5 (10 nM) (D). ECL1(C) inverso at 15 µM does not induce the migration of any of the HEK cells tested. ECL1 (C) inverso inhibits the migration of mouse monocytes (CD11b$^+$ Ly6G$^-$) (E) and classical monocytes (CD11b$^+$Ly6G$^-$7/4$^{hi}$) (F) that express CCR2 with an $IC_{50}$ of 2 µM. Data are the mean of three independent triplicates and each bar is an average of triplicates.

Figure 4:
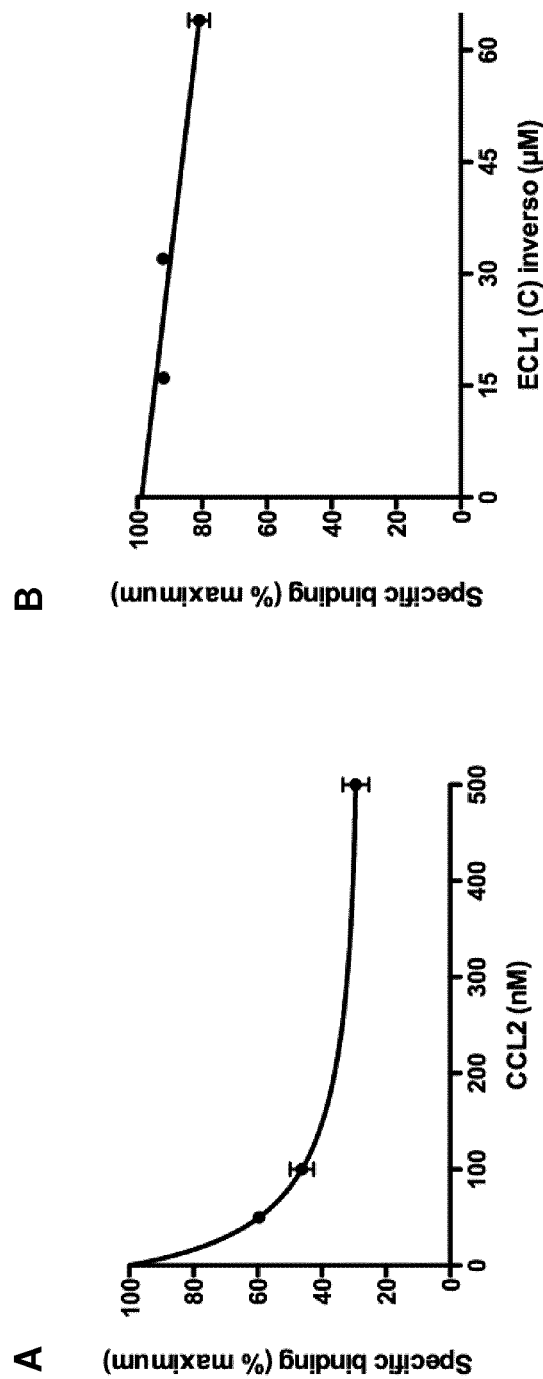

FIG. 4: ECL1 (C) inverso is a non competitive antagonist. (A) CCL2 displaces dose-dependently the binding of CCL2-Alexa-647 with HEK-CCR2. (B) ECL1 (C) inverso at indicated concentrations does not displace the binding of CCL2-Alexa-647 with HEK-CCR2.

Figure 5:
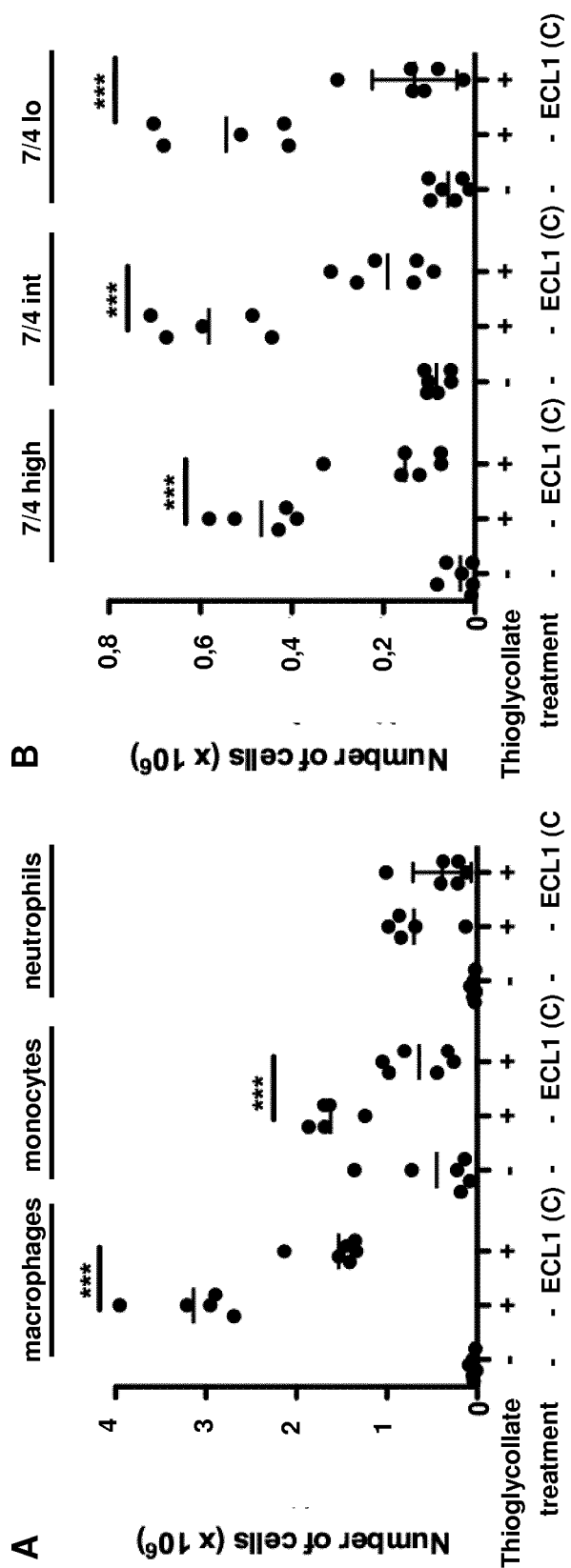

FIG. 5: ECL1 (C) inverso inhibits monocyte infiltration in a non infectious model of peritonitis. After i.p injection of 1 mL of 3% thioglycollate, C57BL/6 mice were treated 14 hours later with ECL1 (C) inverso or control peptide (90 µg/TID). 12 hours after the last injection, mice were sacrified and peritoneal cells were harvested. (A) ECL1 (C) inverso inhibits the recruitment of peritoneal macrophages (CD11b$^+$Ly6G$^-$F4/80$^+$), monocytes (CD11b$^+$Ly6G$^-$F4/80$^-$) but not neutrophils (CD11b$^+$Ly6G$^+$). (B) ECL1 (C) inverso has an inhibitory effect on the recruitment of all monocyte subsets defined as (7/4$^{hi}$, 7/4$^{int}$ and 7/4$^{lo}$). n=6 mice per group and experiments were done three times.

Figures 6, 7:
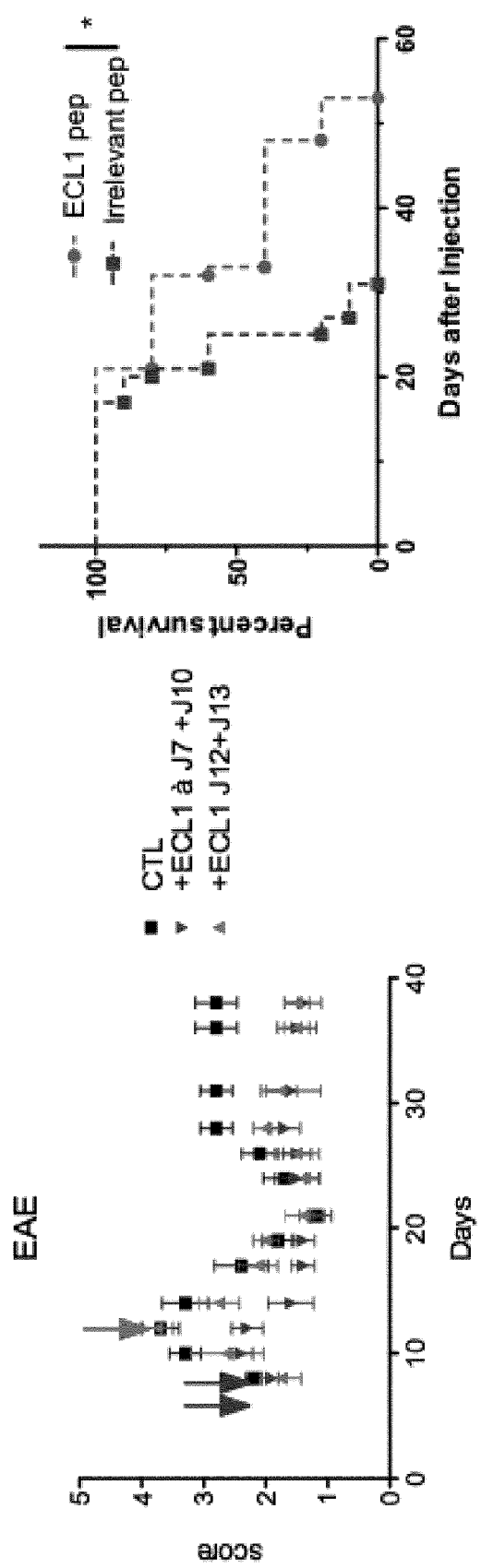
Figure 9A:
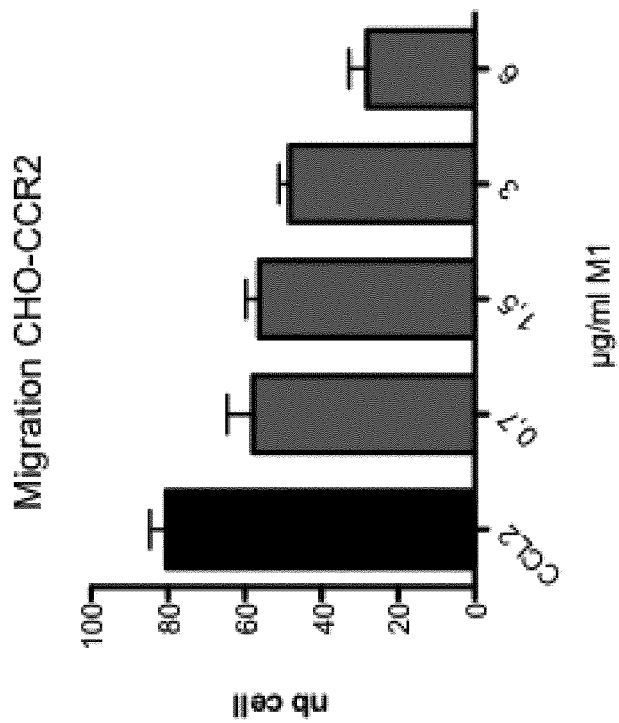

FIG. 6: ECL1 (C) inverso reduces severity of clinical symptoms and prevents relapses in a model of multiple sclerosis. Clinical signs of EAE were assessed daily by the following scoring system: 0, no signs; 1, hindlimb weakness; 2, hindlimb weakness and tail paralysis; 3, hindlimb and tail paralysis; 4, hindlimb and tail paralysis and forelimb weakness; 5, moribund; and 6, death. Mice received 2 intraperitoneal injections of 90 µg of ECL-1 ECL1 (C) inverso at the time indicated on the figure. The control groups received either PBS alone or scramble peptide are the same concentration as ECL1 (C) inverso.

FIG. 7: ECL1 (C) inverso extends the survival of mice developing liver metastasis. EL4 lymphoma cells were injected i.v. and mice survival was monitored. ECL1 (C) inverso (90 µg/mouse/injection) or irrelevant peptide were injected i.p. starting day 12 after tumor inoculation 3 time a week until day 23.

Figure 8:
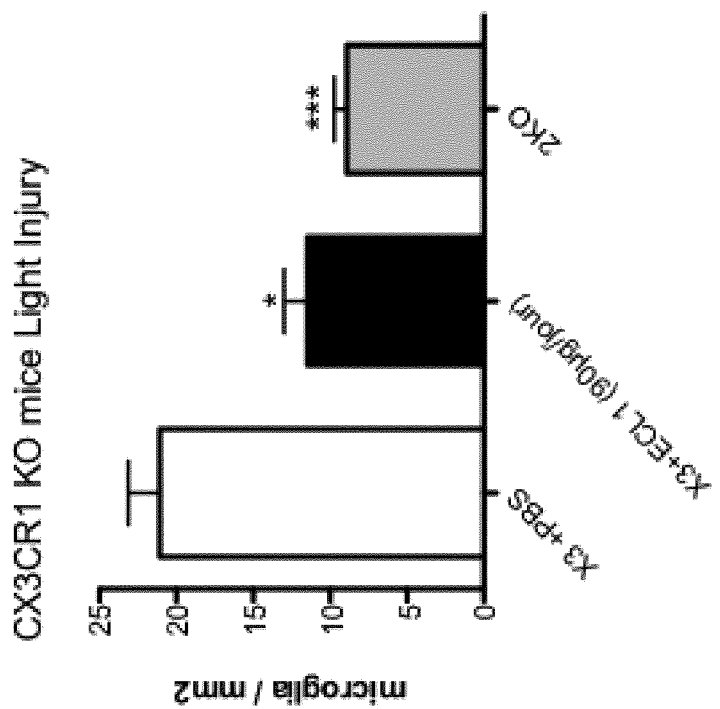
Figure 9C:
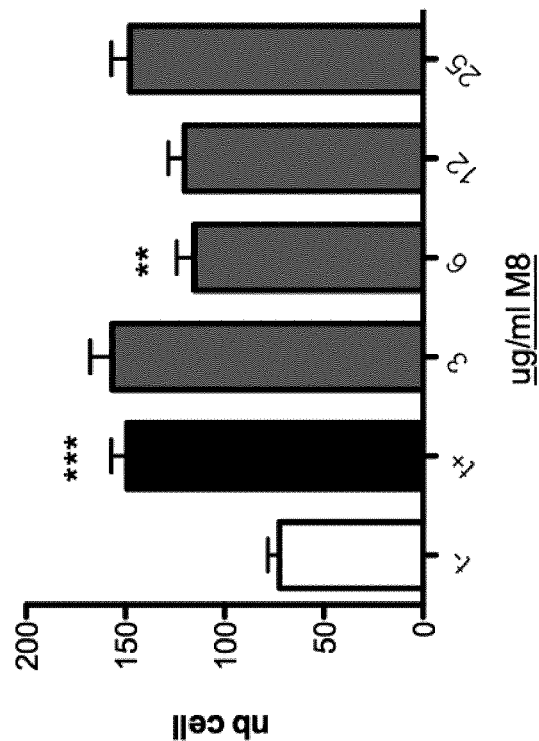
Figure 9B:
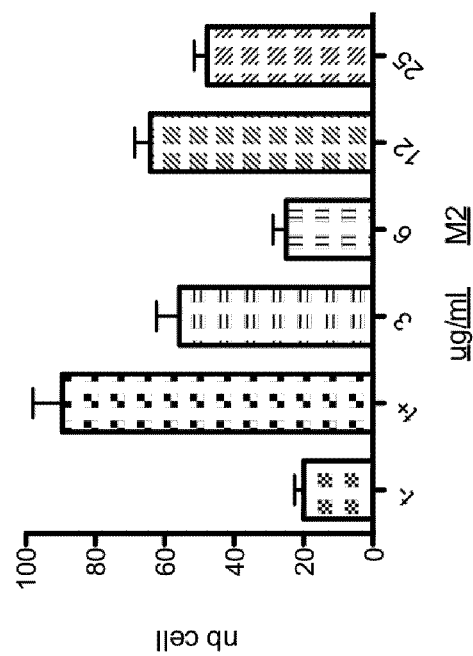
Figure 9D:
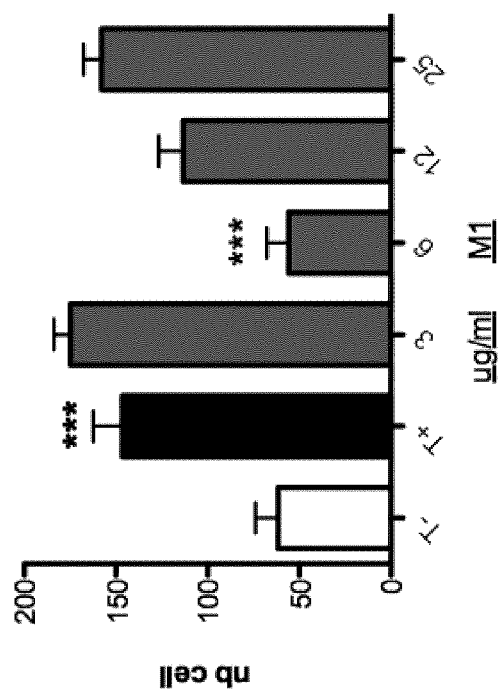

FIG. 8: ECL1 (C) inverso reduces the accumulation of microglial cells in sub-retinal space. in retinal degeneration. Mice models of retinal degeneration were tested with ECL1 (C) inverso peptide, as explained in Example 4. Microglial cells (MC) accumulation and retinal degeneration were assessed.

FIGS. 9A, 9B, 9C, 9D show the results of chemotaxis inhibition by peptides ECL1, M2, M8 and M1, respectively, as explained in Example 5. t-=negative control (saline solution); t+=positive control (CCL2, natural agonist of CCR2)

DETAILED DESCRIPTION OF THE INVENTION

Definitions

The term "patient" or "subject" refers to a human or non human animal, preferably a mammal, including male, female, adult and children. The patient is in need of a treatment wherein a pro-apoptotic and/or anti-inflammatory effect is desired. Preferably it means typically a patient with CCR2 mediated syndrome, disorder or disease, who is especially a patient with a syndrome, disorder or disease that is associated with elevated CCL2 expression or CCL2 overexpression, or a patient with an inflammatory condition that accompanies syndromes, disorders or diseases associated with elevated CCL2 expression or CCL2 overexpression.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment refers to any of: halting the onset, reducing the risk of development, reducing the incidence, delaying the onset, reducing the development, as well as increasing the time to onset of symptoms of a particular disorder.

The term "composition" or "pharmaceutical composition" means a product comprising the specified ingredients in the specified amounts, as well as any product which results, directly or indirectly, from such combinations of the specified ingredients in the specified amounts and one or more pharmaceutically acceptable carriers therefor.

The term <<medicament>>, means a product for use in the medical diagnosis, cure, treatment or prevention of disease(s), such a disease, within the scope of the present description, may be a CCR2 mediated syndrome or disorder.

The term "pharmaceutically acceptable carrier" means molecular entities that are of sufficient purity and quality for use in the formulation of a composition or medicament of the invention and that, when appropriately administered to an animal or a human, do not produce an adverse, allergic, of other untoward reaction. Since both human and veterinary use is included within the scope of the invention, a pharmaceutically acceptable formulation includes a composition or medicament for either human or veterinary use.

The term "effective amount" means that amount of active ingredient (especially the peptide or compound of the invention) that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

The term "CCR2 mediated syndrome, disorder" means, without limitation, syndromes, disorders or diseases associated with elevated CCL2 expression, CCL2 overexpression or inflammatory conditions that accompany syndromes, disorders or diseases associated with elevated CCL2 expression or CCL2 overexpression.

The terms "elevated CCL2 expression" or "CCL2 overexpression" mean unregulated or up-regulated CCR2 activation as a result of CCL2 binding, especially in comparison with a control that is preferably a healthy patient.

The term "unregulated" means unwanted CCR2 activation in a multicellular organism resulting in harm (such as discomfort or decreased life expectancy) to the multicellular organism The term "up-regulated" means: 1). increased or unregulated CCR2 activity or expression, or 2). increased CCR2 expression leading to unwanted monocyte and lymphocyte migration, especially in comparison with a control that is preferably a healthy patient. The existence of an inappropriate or abnormal level of CCL2 or activity of CCR2 is determined by procedures well known in the art.

The term "conservative substitution" as used herein denotes the replacement of an amino acid residue by another, without altering the overall conformation and biological activity of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine. By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Peptide Preparation:

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Peptide Characteristics:

Optionally sequence SEQ ID NO:1 may be extended by one or several amino-acids, for instance 1 to 20 aminoacids, preferably between 1 and 14 aminoacids, or for instance 1, 2, 3, 4, 5, 6, 7, 8, 9 or 10 amino acids.

A preferred peptide of the invention shows sequence

X1-TFLKC-X2, (SEQ ID NO: 2)

wherein X1 is absent, is glycine or represents an amino acid sequence selected from the group consisting of AG, LG, YLG, and HYLG (SEQ ID NO: 30);

and X2 independently is absent, is methionine, or represents an amino acid sequence selected from the group consisting of MA, MAN, MANG (SEQ ID NO: 24), MANGF (SEQ ID NO: 25), MANGFV (SEQ ID NO: 26), MANGFVW (SEQ ID NO: 27), MANGFVWE (SEQ ID NO: 28), and MANGFVWEN (SEQ ID NO: 29).

The peptide of the invention comprises
amino acid sequence Thr-Phe-Leu-Lys (SEQ ID NO:17).
a sequence deriving from SEQ ID NO:17 by one or more chemical modifications that confer resistance to proteolysis;
or a sequence deriving from SEQ ID NO:17 by one or more conservative substitutions.

A preferred peptide of the invention consists

X1-TFLK-X3, (SEQ ID NO: 18)

wherein X1 is absent, is glycine or represents an amino acid sequence selected from the group consisting of AG, LG, YLG, and HYLG (SEQ ID NO: 30);
and X3 independently is absent, or is alanine
or a sequence deriving from SEQ ID NO:18 by one or more chemical modifications that confer resistance to proteolysis;
or a sequence deriving from SEQ ID NO:18 by one or more conservative substitutions.

Particular peptides of the invention are selected from the group consisting of

LGTFLKC, (SEQ ID NO: 3)

HYLGTFLKCMA, (SEQ ID NO: 4)

LGTFLKCMA, (SEQ ID NO: 5)

HYLGTFLKC, (SEQ ID NO: 6)

GTFLKCMANGF, (SEQ ID NO: 7)

TFLKCMANGFV, (SEQ ID NO: 8)

HYLGTFLKCMANGFVWEN; (SEQ ID NO: 9)

LGTFLK (SEQ ID NO: 19)

AGTFLKC (SEQ ID NO: 20)

LGTFLKA (SEQ ID NO: 21)

GTFLK (SEQ ID NO: 22)

AGTFLKA. (SEQ ID NO: 23)

The peptide consisting of of SEQ ID NO: 3 is preferred.

Preferably the peptide of the invention consists of a peptide of no more than 18 aminoacids, preferably no more than 15, 14, 13, 12, 11, 10, 9, or 8 aminoacids, typically no more than 10 aminoacids.

Also encompassed are proteolysis-resistant peptides deriving from SEQ ID NO: 1 to 9 or 19 to 23 by one or more chemical modifications, or substantially homologous peptides deriving from sequence SEQ ID NO: 1 to 9 or 19 to 23 by one or more conservative substitutions.

In a particular embodiment, the proteolysis-resistant peptides or homologous peptides still show the core TFLK sequence.

In a preferred embodiment, the proteolysis-resistant peptides or homologous peptides exhibit substantially the same biological properties as the peptides from which they derive. Especially the peptides of the invention reduce CCL2 induced monocyte chemotaxis, preferably with an IC50 for reduction in CCL2 induced monocyte chemotaxis of between about 5 µM to about 5 nM, preferably in the nanomolar range, still preferably about 1 nM. They reduce CCL2 intracellular calcium mobilization with an IC50 for reduction in CCL2 induced intracellular calcium mobilization of between about 5 µM to about 5 nM, preferably about 0.75 µM or 1 nM, or more generally in the nanomolar range.

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

The peptides of the invention may be composed of amino acid(s) in D configuration, which render the peptides resistant to proteolysis. Alternatively all or part of the aminoacids may be in L configuration.

Noteworthy, the peptides originally tested were in the all D-configuration simply as a matter of convenience, as such peptides typically tend to be less susceptible to hydrolysis or proteolysis, particularly in vivo. However, the skilled person would understand that corresponding peptides comprising naturally occurring L-amino acids, or a mixture of D- and L-amino acids, share significant structural/conformational similarity with the all D peptides, and are expected to possess CCR2 inhibiting activity as well.

The peptides may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called "staple" technology described in Walensky et al, Science, 2004, 305:1466-1470.

All these proteolysis-resistant chemically-modified peptides are encompassed in the present invention.

Also encompassed are substantially homologous peptides deriving from sequence (I) by one or more conservative substitutions. Preferably, these homologous peptides do not include two cysteine residues, so that cyclization is prevented. Two amino acid sequences are "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.).

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Therapeutic Indications

The peptides of the invention are useful therapeutic agents, as CCR2 antagonists.

A subject of the invention is thus a pharmaceutical composition or medicament that contains such peptide or compound, alone or in combination.

The peptides of the invention reduce CCL2 induced monocyte chemotaxis, preferably with an IC50 for reduction in CCL2 induced monocyte chemotaxis of between about 5 µM to about 5 nM, preferably in the nanomolar range, still preferably about 1 nM.

They reduce CCL2 intracellular calcium mobilization with an IC50 for reduction in CCL2 induced intracellular calcium mobilization of between about 5 µM to about 5 nM, preferably about 0.75 µM or 1 nM, or more generally in the nanomolar range.

Accordingly, the peptides or compounds of the invention are useful in a method for preventing, treating or ameliorating a CCR2 mediated disorder, such as a CCR2 inflammatory syndrome, disorder or disease.

It is thus provided a method for treating a CCR2 mediated syndrome, disorder or disease in a subject in need thereof comprising administering to the subject an effective amount of a peptide or compound of the invention.

The effective amount of the peptide or compound in such a therapeutic method may be typically from about 0.001 mg/kg/day to about 300 mg/kg/day, or from about 50 µg to 20 g daily.

The invention includes the use of peptide or compound as described herein for the preparation of a composition or medicament for treating a CCR2 mediated syndrome, disorder or disease in a subject in need thereof, wherein the composition or medicament comprises a peptide or compound of the invention with a pharmaceutically acceptable carrier.

CCR2 mediated syndromes, disorders or diseases include, without limitation, ophthalmic disorders, uveitis, atherosclerosis, rheumatoid arthritis, psoriasis, psoriatic arthritis, atopic dermatitis, multiple sclerosis, Crohn's Disease, ulcerative colitis, nephritis, organ allograft rejection, fibroid lung, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive staphyloccocia, inflammation after cataract surgery, allergic rhinitis, allergic conjunctivitis, chronic urticaria, asthma, allergic asthma, periodontal diseases, periodontitis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach.

In a particular embodiment, the peptide of the invention is useful for treating age-related macular degeneration or retinal degeneration.

In another embodiment, the peptide of the invention is useful for preventing treating a cardiovascular disease, especially preventing or treating atherogenesis or ischemia of lower members or of the heart.

In still another embodiment, the peptide of the invention is useful in treating pain, in particular peripheral pain, such as pain from the sciatic nerve.

The invention includes a method for preventing, treating or ameliorating a CCR2 mediated inflammatory syndrome, disorder or disease in a subject in need thereof comprising administering to the subject an effective amount of a peptide as described herein in a combination therapy with one or more anti-inflammatory agents (such as a small molecule, antibiotic, corticosteroid, steroid, and the like), anti-infective agents or immunosuppressive agents.

Pharmaceutical Compositions:

The peptide may be administered by any convenient route including intravenous, oral, transdermal, subcutaneous, mucosal, intramuscular, intrapulmonary, ocular, intranasal, parenteral, rectal, vaginal and topical. Injection into the vitreous body of the eye is of particular interest, especially for treating age-related macular degeneration or retinal degeneration.

The peptide is typically formulated in association with a pharmaceutically acceptable carrier.

The composition or medicament comprising the peptide or compound of the invention may be in a dosage unit such as a tablet, pill, capsule, powder, granule, liposome, biodegradable carrier, ion exchange resin, sterile solution and the like (facilitating immediate release, timed release, or sustained release), parenteral solution or suspension, metered aerosol or liquid spray, drop, ampoule, auto-injector device or suppository.

Compositions or medicaments suitable for oral administration include solid forms such as pills, tablets, caplets, capsules (each including immediate release, timed release, and sustained release formulations), granules and powders and liquid forms such as solutions, syrups, elixirs, emulsions and suspensions. Forms useful for nasal administration include sterile solutions or nasal delivery devices. Forms useful for ocular administration include sterile solutions or ocular delivery devices. Forms useful for parenteral administration include sterile solutions, emulsions and suspensions.

The dosing is selected by the skilled person so that an effect is achieved, and depends on the route of administration and the dosage form that is used The composition or medicament may contain an effective amount of from about 0.001 mg to about 5000 mg (preferably, from about 0.001 to about 500 mg) of a peptide of the invention.

A contemplated range of the effective amount includes from about 0.001 mg to about 300 mg/kg of body weight per day. A contemplated range also includes from about 0.003 to about 100 mg/kg of body weight per day. Another contemplated range includes from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250, and 500 milligrams of the active peptide for the symptomatic adjustment of the dosage to the patient to be treated. Optimal dosages will vary depending on factors associated with the particular patient being treated (e.g., age, weight, diet, and time of administration), the severity of the condition being treated, the compound being employed, the mode of administration, and the strength of the preparation. The use of either daily administration or post-periodic dosing may be employed.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette. Preferably the compositions are sterile and aqueous based, using purified water.

Further aspects and advantages of the present invention will be disclosed in the following experimental section, which should be regarded as illustrative and not limiting the scope of the present application.

EXAMPLES

Example 1

Design and Test of "ECL1 (C) Inverso" Peptide

CCR2 juxtamembranous and transmembranous regions were determined by using PredictProtein, Protscale and Prosite software. Flexibility and hydrophobicity profiles were also determined with the sames softwares. CCR2 3D structure was modelized by using rhodopsin as a template and visualized with MOE (Molecular operating Environment; Montreal, Canada). Peptides were derived from the human primary sequence of CCR2 and a BLAST analysis was performed to insure specificity of sequence.

Materials and Methods
Peptide Synthesis

The synthesis of ECL1 (C) inverso was carried out by a solid phase Fastmoc chemistry procedure on an Applied Biosystems 433A Automated Peptide Synthesizer (Applera, France). Resins and Fmoc-protected amino acids were purchased from Merck Chemicals (Novabiochem, UK) and solvents from SdS (France) as previously described (Vanhoye et al., 2004 Biochemistry, 43(26):8391-409). All amino acids were D-amino acids. The Fmoc-Leu-Wang resin (100-200 mesh) was used for ECL1 (C) inverso. Briefly, ECL1 (C) inverso synthesis products were cleaved from the resin by a mixture of trifluoracetic acid (TFA) (94%), H2O (2.5%) Triisopropylsilan (TIS) (2.5%), precipitated in ether, centrifuged and lyophilized. Peptides were purified by a RP-HPLC (C18 reverse-phase column, PrepLC 25 mm module, 250 mm×100 mm, 15 mm particle Waters) on a Waters 1252 Binary HPLC pump (flow rate 8 ml·min-1). Purity was assessed analytical RP-HPLC (C18 column, 5 µm, Luna C18(2), 4.6 mm×250 mm, 100 Å pore diameter, Phenomenex) on a Waters 1252 Binary HPLC pump (flow rate 0.75 ml·min-1) and by MALDI-TOF mass spectrometry (Voyager DE-PRO, Applied Biosystems).

Cell Culture

Native and stably expressing CCR2, CX3CR1, CCR1 or CCR5 HEK293 or CHO cells were cultured in DMEM supplemented with 2 mM L-glutamine, 1% non-essential amino acids, 2 mM sodium pyruvate, 10% FBS, penicillin (50 U/mL), and streptomycin (50 µg/mL). All HEK or CHO cells expressing chemokine receptors were described previously. HEK- or CHO-CCR2, -CCR5, -CX3CR1 and were grown in the presence of G418 (200 µg/mL) and HEK-CCR1 in the presence of hygromycin (100 µg/mL). Mouse bone marrow cells (MBMC) were obtained from C57BL/6 mice.

Animals 10-week-old male or female C57BL/6 mice were kept in pathogen-free conditions with food and water available ad libitum and housed in a 12 h light/12 h dark (100-500 lux) cycle.

Binding Assay
Radioligand Binding Assays

Binding assay was carried out using I125-CCL2 (specific activity 2200 Ci/mmol; Perkin elmer, inc.). 300,000 HEK cells stably expressing CCR2 and native cells were incubated with I125-CCL2 in the presence or absence of recombinant human CCL2 (10 nM or 100 nM) or ECL1 (C) inverso (1-10-30 µM) in 200 µl buffer (PBS containing 0.5% BSA and 0.01% HEPES). After 1 h incubation at 37° C., cells were washed three times with 1 ml of cold washing solution. Gamma emissions were then counted in the cell pellet with gamma counter. Non-specific binding represented less than 15% of total binding and was subtracted from total binding to define specific I125-CCL2 binding.

CCL2-Alexa 647 Binding Assay

Binding was performed with the same cells. 200,000 cells were pre-incubated for 30 minutes at 4° C. in 100 µl buffer (PBS containing 0.5% BSA, 0.2% EDTA and NaN3 0.01%) with recombinant human CCL2 (50 nM, 100 nM and 500 nM), ECL1 (C) inverso (11.3 µM, 28.2 µM and 56.3 µM) or with buffer. After, 50 nM CCL2-alexa 647 (Almac) were add for 30 minutes at 4° C. and washed three times with 1 ml of cold buffer. Cells were incubated with 10 µl anti-human-CCR2 (BD pharmingen) for 30 minutes at 4° C. in the dark and washed three times with 1 ml of cold buffer. Cells and beads were counted on FACSCalibur flow cytometer and data were analysed with FlowJo software.

Bioluminescence Resonance Energy Transfer Assay (BRET)

Cells were seeded at a density of 100,000 cells/well in a 12-well dishes 24 h before transfection. Transient transfections were performed with the cationic polymer transfection reagent, JePEI (Polyplus transfection, Ozyme) in 150 mM NaCl. 0.5 µg of various CCR2-pRluc constructs were transfected alone or with 2.5 µg of various CCR2-pEYFP constructs. After overnight incubation, the transfected cells were detached with phosphate-buffered saline (PBS) and washed with HBSS buffer supplemented with 10 mM HEPES, 1 mM CaCl2, and 0.5 mM MgCl2. A cell homogenate was harvested and seeded in a 96-well black plate (Perkin Elmer) in 100 µL of supplemented HBSS. Coelenterazine H (Interchim, Montlugon, France) was added to reach 5 µM. ECL1 (c) inverso and control peptides were incubated 15 min before reading. Readings were measured with a microplate analyzer (Fusion; PerkinElmer) that allowed the sequential integration of signals detected in the 485±20 nm window for luciferase and the 540±20 nm window for yellow fluorescence protein (YFP) light emissions. The BRET signal was determined by calculating the ratio of the light intensity emitted by the CCR2-YFP over the light intensity emitted by the CCR2-Luciferase (Luc). The values were corrected by substracting the background BRET signal detected when the CCR2-Luc construct was expressed alone. The values are the mean over 15 measurements.

Calcium Flux Assay

Cytosolic-free calcium assay was measured by fluorescent detection with the HitHunter™ Calcium No WashPLUS (Ca NWPLUS) assay kit (DiscoveRex, #90-0091). Briefly, HEK or CHO expressing the chemokine receptor of interest (5.104) were plated overnight at 37° C., 5% CO2 before pre-loading with a calcium sensitive dye (Ca NWPLUS working reagent) supplemented with probenecid (Sigma-Aldrich, #P8761) to avoid calcium dye leakage from the cells, for 1 h at 37° C. Cells were then treated with control buffer or peptides at various concentrations and appropriate agonist. Signal was measured as function of time on a fluorescent plate reader equipped with fluidic handling (FlexStation 3, Molecular Devices). Maximum change in fluorescence over baseline (peak signal) was used to determine agonist response, as quantified using SoftMax Pro software. All experiments were run in triplicate, and results are representative of at least three independent experiments.

β-Arrestin Assay

Recruitment of β-arrestin in live cells was measured by chemoluminescence detection with the PathHunter™ eXpress β-Arrestin assay kit (DiscoveRex, #93-00446E1). Briefly, 100 μL PathHunter eXpress cells were expressing CCR2 were plated on a 96-well tissue culture treated plate for 48 hours at 37° C., 5% CO2. Cells were first incubated with ECL1 (C) inverso or control peptide and before adding 10 μL of the agonist, CCL2 diluted in OCC medium to achieve the EC80 determined beforehand or with OCC medium alone, for respectively 60 and 90 min at 37° C., 5% CO2. The reaction was stopped by adding 55 μL of the Working Detection Reagent Solution (PathHunter detection reagent) for 90 min at Room temperature. Chemoluminescent signal was read on a luminescent plate reader (TriStar LB 941, Berthold Technologies, Thoiry, France). Assays were run in triplicates.

Migration Assay

Migration assays were performed in 24-transwell inserts (Corning Costar Avon, France) with 8 μm polycarbonate filter for HEK or CHO cells and 5 μm for MBMC. Cells were resuspended in chemotaxis buffer (5.105 cells in 100 μl RPMI containing 0.5% BSA and 10 nM HEPES) in presence or not of ECL1 (C) inverso at appropriate concentration and located in the top chamber. The bottom of each well was filled with 600 μL pre-warmed chemotaxis buffer at indicated chemokine concentration. The plates were then incubated for 4 hours at 37° C. in a 5% CO2 atmosphere. Cells that passed the membrane were counted by FACSCalibur flow cytometry with a pre-determined number of beads (Polybead, carboxylate microsphere Polyscience, Inc) added to the tube. Before counting the cells by flow cytometry, mouse leukocytes were immunophenotyped with a mix of fluorescent antibodies (anti-mouse Ly6G-PE, anti-mouse NK1.1-PE, anti-mouse CD1b-PCP, anti-mouse 714-FITC, BD Biosciences) and HEK expressing chemokine receptors with appropriate fluorescent anti-human chemokine receptor. Data were analysed with FlowJo software and results are expressed as a number of cells migrating in the presence or in the absence of chemoattractant. Experiments were run in triplicate, and results are representative of at least three independent experiments.

Cytotoxicity

Cytotoxicity of ECL1 (C) inverso was tested by incubating 5.105 mouse leukocytes in 100 μl RPMI containing 0.5% BSA and 10 nM HEPES with ECL1 (C) inverso or control peptide for 4 hours at 37° C., 5% CO2. Cells were immunophenotyped by adding a mix of fluorescent antibodies (anti LY-6G-PE, anti CD11b-PerCP, anti 714-FITC, anti F4/80-APC, anti NK-PE) and counted by FACSCalibur flow cytometry with predetermined number of beads (Polybead, carboxylate microsphere Polyscience, Inc) added to the samples. Data were analyzed with FlowJo.

Thioglycollate-Induced Peritoneal Inflammation

C57BL/6 mice were injected i.p with 1 mL 3% (wt/vol) thioglycollate (Sigma-Aldrich, I'lle d'Abeau, France) and dissolved in sterile PBS and then 14, 19 and 24 hours later injected i.p. with ECL1 (C) inverso or control peptide (30 μg). 12 hours after the last injection, mice were killed and 3 mL of cold PBS was injected i.p. to harvest peritoneal cells which were then stained with anti-mouse Ly6G-PE, anti-mouse NK1.1-PE, anti-mouse CD11b-PCP, anti-mouse 7/4-FITC and anti F4/80-APC (BD Biosciences). Cells and beads were then counted by FACSCalibur flow cytometry and data were analyzed with FlowJo. Cells being CD11bhiLy6G−NK1.1− were considered to be monocytes, and subsets discrimination was made upon 7/4 expression. 7/4 expression has been shown to be equivalent to Ly6C expression on monocyte subsets.

Results

Screening of peptides derived from extracellular juxtamembranous regions

The inventors designed a series of small peptides between 5 and 7 amino acids which reproduced the extracellular juxtamembranous regions of CCR2. All the peptides were synthesized with D-amino acids in order to increase their stability for further in vivo use. Peptides were screened for their ability to inhibit CCL2-induced calcium release, which is classically associated to GPCR stimulation.

The sequence of these peptides is shown below:

| Peptide | Sequence |
|---|---|
| ECL1 (C) | CKLFTGL (SEQ ID NO: 10) |
| ECL1 (C) inverso | LGTFLKC (SEQ ID NO: 3) |
| ECL2 (N) | LFTKC (SEQ ID NO: 11) |
| ECL2 (N) inverso | CKTFL (SEQ ID NO: 12) |
| ECL3 (C) | HTLMRNL (SEQ ID NO: 13) |
| ECL3 (C) inverso | LNRMLTH (SEQ ID NO: 14) |
| ECL3 (N) | LNTFQEF (SEQ ID NO: 15) |
| ECL3 inverso | FEQFTNL (SEQ ID NO: 16) |

Before testing the peptides, the inventors first confirmed that CCL2 elicited calcium release on HEK-CCR2 cells with an EC80 value of 50 nM. Among all the peptides tested, the heptapeptide LGTFLKC (SEQ ID NO: 3), named ECL1 (C) inverso, presented the most interesting properties by abolishing dose-dependently the calcium response induced by 50 nM CCL2, with an IC50 value of 0.75 μM (FIG. 1A). These results were confirmed by testing the recruitment of β-arrestin in live cells, which is another event coupled to GPCRs. As shown on FIG. 1B, CCL2 could induce the recruitment of β-arrestin in HEK-CCR2 with an EC80 value of 12.5 nM and this recruitment could be inhibited by adding ECL1 (C) inverso with an IC50 value of 2 μM. The inventors also observed that unlike CCL2, ECL1 (C) inverso could not induce significant calcium response or β-arrestin recruitment at concentrations up to 500 μM in HEK-CCR2 cells but also in CHO-CCR2.

Figure 2B:
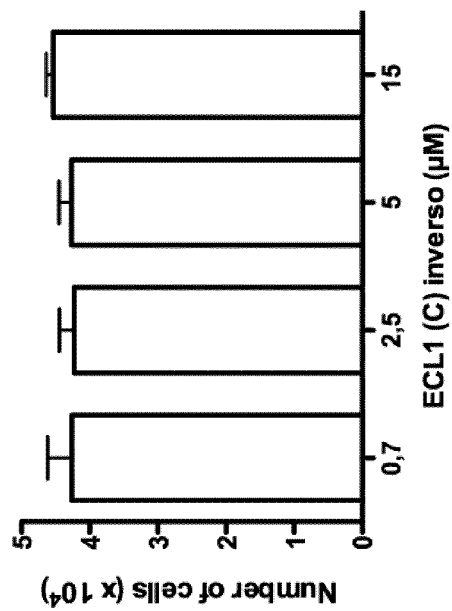
Figure 2A:
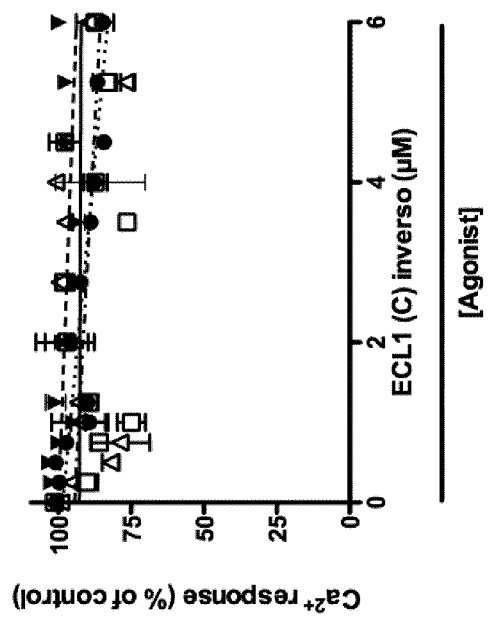

Chemotactic and Calcium-Flux Responses Induced by CCL2 are Specifically Inhibited by ECL1 (C) Inverso The inventors evaluated the selectivity of ECL1 (C) inverso for CCR2 by testing its inhibitory effect on the calcium response on other chemokine receptors, CCR1, CCR5 and CX3CR1 which sequences are closely related to the one of CCR2 and also on other GPCRs, like the lypophosphatic acid (LPA)-GPCR. In contrast to the inhibitory effect of ECL1 (C) inverso on the calcium release induced by CCL2 on HEK-CCR2, no significant inhibition was observed on calcium release induced by CCL5 (25 nM) on HEK-CCR5 and HEK-CCR1, CX3CL1 (20 nM) on HEK-CX3CR1 or by LPA (10 µM) or ATP (30 µM) on HEK cells (FIG. 2A). The inventors also confirmed that inhibition of CCL2-induced calcium release by ECL1 (C) inverso was not due to cytotoxicity. For this, we incubated HEK-CCR2 or MBCM in presence of ECL1 (C) at various concentrations (FIG. 2B). After 4 hours of incubation, no significant cell death could be observed.

The inventors then investigated the effect of ECL1 (C) inverso on CCR2-mediated chemotaxis. HEK-CCR2 migrated upon CCL2 at a concentration of 100 nM. ECL1 (C) inverso inhibited this CCL2-dependent chemotaxis in a dose-dependent manner with an IC50 value of 2 µM (FIG. 3A). Similar results were obtained with monocytes, macrophages (FIG. 3E) and NK cells MBMC or CHO-CCR2. Moreover, ECL1 (C) inverso inhibited CCL2-mediated chemotaxis of inflammatory monocytes (CD11b+Ly6G−7/4hiCCR2+) (FIG. 3F) but did not have any effect on resident monocytes (CD11b+Ly6G−7/4loCCR2−) (data not shown). On the contrary, ECL1 (C) inverso did not antagonize the chemotaxis effect induced by CCL5 (10 nM) or CX3CL1 (1 nM) on, respectively, HEK-CCR5 or -CCR1 or HEK-CX3CR1 (FIGS. 3B, C, D).

ECL1 (C) at concentrations up to 500 µM did not induced chemotaxis of either HEK-CCR2, -CCR5, -CX3CR1 or mouse leukocytes.

All together these results indicate that ECL1 (C) inverso is a specific CCR2 antagonist that inhibit calcium and chemotactic response.

Characterisation of ECL1 (C) Inverso as a Non Competitive Antagonist

To further characterize this new CCR2 antagonist, the inventors tested whether ECL1 (C) inverso bound to the same CCR2 site as CCL2. For this, the binding affinity of ECL1 (C) inverso for CCR2 was compared with that of native CCL2 in a competition binding with HEK-CCR2 cells and [125I]-CCL2 or CCL2 coupled to a fluorescent (Alexa-647) as tracer. As shown FIGS. 4A and B, whereas CCL2 could displace dose-dependently bound [125I]-CCL2 or CCL2-Alexa 647, ECL1 (C) inverso could not, indicating that ECL1 (C) inverso did not bound at the same binding site as the natural ligand CCL2.

All together these results indicate that ECL1 (C) inverso is a non competitive antagonist.

ECL1 (C) Inverso Inhibits the Recruitment of Leukocytes In Vivo

The in vivo antagonist effect of ECL1 (C) inverso, as a potential therapeutic anti-inflammatory treatment, was first evaluated in the non infectious peritonitis model. 14 hours before treating C57BL/6 mice with either ECL1 (C) inverso or with a control peptide, a sever inflammation was created by a thioglycollate injection i.p. injected. Mice were sacrificed 12 hours after the last injection of peptide. The recruitment of leukocytes into the peritoneal cavity was analyzed by flow cytometry. As shown FIG. 5A, monocytes (CD11b+Ly6G−F4/80−), macrophages (CD11b+Ly6G−F4/80+) and neutrophils were recruited in the peritoneal cavity after thioglycollate injection. The recruitment of monocytes and macrophages was strongly inhibited after treatment with 90 µg of ECL1 (C) inverso injected i.p. TID, but not with control peptide. Surprisingly, it also decreased the recruitment of neutrophils, albeit in a lesser extent, suggesting an indirect inhibitory mechanism on neutrophils as they do not express CCR2. A closer analysis (FIG. 5B) also showed that all monocytes populations ("inflammatory" 7/4 hi CCR2+ and "resident" 7/4 lo CCR2− monocytes) were affected by the inhibitory effect of ECL1 (C) inverso indicating an inter-dependent effect between the population.

Example 2

ECL1 (C) Inverso in a Model of Multiple Sclerosis

Experimental autoimmune encephalomyelitis (EAE) in mice is the recognized animal model of multiple sclerosis (an inflammatory disease that involves CCR2). Mice that are invalidated with CCR2 does not develop the disease.

EAE induction was adapted from Ephrem et al, Blood 2008 Jan. 15; 111(2):715-22.

C57BL/6J mice (weighing approximately 20 g) were immunized with 200 µg MOG35-55 peptide (fragment 35-55 of MOG protein) emulsified in Complete Freund's Adjuvant (CFA; Sigma-Aldrich, St. Quentin Fallavier, France) 1:1 by volume containing 800 µg of nonviable desiccated *Mycobacterium tuberculosis* H37RA (Difco Laboratories, L'Arbresk, France). A final volume of 200 µL was injected subcutaneously at 4 sites over the flanks. In addition, 300 ng of Pertussis toxin (List Biologic Laboratories, Meudon, France) was given intravenously on the same day and 2 days later. Clinical signs of EAE were assessed daily by the following scoring system: 0, no signs; 1, hindlimb weakness; 2, hindlimb weakness and tail paralysis; 3, hindlimb and tail paralysis; 4, hindlimb and tail paralysis and forelimb weakness; 5, moribund; and 6, death. Mice received 2 intraperitoneal injections of 90 µg of ECL1 (C) inverso at the time indicated on FIG. 6. The control groups received either PBS alone or scramble peptide ar the same concentration as ECL1 (C) inverso.

As shown on FIG. 6, injection of ECL1 (C) inverso in course of the disease progression (days 7 and 8) reduces severity of clinical symptoms. Injection of ECL1 (C) inverso at disease peak (days 12 and 13) prevents relapse.

Example 3

ECL1 (C) Inverso in Treating Cancer

The microenvironment of tumors comprises macrophages that derive from circulating monocytes. Diminishing the infiltrating macrophages is associated with a better prognosis in patients.

In that context, injections of ECL1 (C) inverso were tested in a murine model of tumor metastatis.

For that purpose EL4 lymphoma cells were injected i.v. and mice survival was monitored. ECL1 (C) inverso (90 µg/mouse/injection) or irrelevant peptide were injected i.p. starting day 12 after tumor inoculation 3 time a week until day 23.

As shown on FIG. 7, injections of ECL1 (C) inverso extended the survival of mice developing liver metastasis.

Example 4

ECL1 (C) Inverso in Treating Retinal Degeneration

Light-induced retinal degeneration, that is a model for age-related macular degeneration, is associated with a sub-retinal CCR2-dependent infiltration of blood monocytes.

Mice models of retinal degeneration were tested with ECL1 (C) inverso peptide.

Two- to four-month-old CX3CR1 KO mice were adapted to darkness for 6 h and pupils were fully dilated with 1% Atropin (Novartis). Animals were then exposed to green LED light (4500 Lux, JP Vezon équipements) for 4 days and subsequently kept in cyclic 12 h/12 h normal animal facility conditions. Microglial cells (MC) accumulation and retinal degeneration were assessed respectively at 10 days after light exposure. Mice were treated daily during green-light exposition with an ECL-1 (90 µg/mouse) or PBS.

Eyes were enucleated, fixed in 4% PFA and sectioned at the limbus; the cornea and lens were discarded. The retinas were carefully peeled from the RPE (retinal pigment epithelium)/choroid/sclera. Retinas were fixed for additional 20 min in cold acetone. Retinas and choroids were incubated with anti-Iba1 (Wako Chemicals) followed by secondary antibody anti-rabbit Alexa 488 (Molecular probes). Choroids and retinas were flatmounted and viewed with a fluorescence microscope DM5500B (Leica). MCs were counted on whole RPE/choroidal flatmounts and on the outer segment side of the retina.

As show on FIG. 8, injection of ECL1 (C) inverso reduces the accumulation of microglial cells in sub-retinal space.

Example 5

Design and Test of Other Peptides

Chemotaxis migration assays were performed using several peptides:
Peptide ECL1 (C) inverso: LGTFLKC (SEQ ID NO: 3)
Peptide M1: LGTFLK (SEQ ID NO: 19)
Peptide M2: AGTFLKC (SEQ ID NO: 20)
Peptide M8: LGTFLKA (SEQ ID NO: 21)

Migration assays were performed in 24-transwell inserts (Corning Costar, Avon, France) with 8 µm pore diameter filters for CHO cells, which were resuspended in chemotaxis buffer (150×103 cells in 100 µl DMEM containing 10% FCS) and loaded into the top chamber. The bottom of each well was filled with 600 µl prewarmed chemotaxis buffer at the indicated chemokine concentration. The plates were then incubated for 5 h at 37° C. in a 5% CO2 atmosphere. Results are expressed as a number of cells migrating in the presence versus the absence of chemoattractant. All conditions were run in duplicate, and results are representative of two independent experiments.

FIGS. 9A, 9B, 9C, 9D show the results of chemotaxis inhibition by peptides ECL1 (C) inverso, M2, M8 and M1, respectively.

---

The invention claimed is:

1. A peptide that consists of LGTFLKC (SEQ ID NO:3).

2. The peptide of claim 1, wherein all or part of the amino acids are in D configuration.

3. The peptide of claim 1, wherein all or part of the amino acids are in L configuration.

4. A compound that comprises a peptide as defined in claim 1 linked to at least one non-peptide moiety.

5. The compound of claim 4, wherein the non-peptide moiety is polyethylene gycol.

6. A pharmaceutical composition, comprising the peptide as defined in claim 1, in association with a pharmaceutically acceptable carrier.

* * * * *

SEQUENCE LISTING

```
<160> NUMBER OF SEQ ID NOS: 30

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Thr Phe Leu Lys Cys
1               5

<210> SEQ ID NO 2
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: "Xaa in position 1" is absent, is glycine or
      represents an aminoacid sequence selected from the group
      consisting of LG, YLG, and HYLG
<220> FEATURE:
<221> NAME/KEY: MISC_FEATURE
<222> LOCATION: (7)..(7)
<223> OTHER INFORMATION: "Xaa in position 7" independently is absent, is
      methionine, or represents an aminoacid sequence selected from the
      group consisting of MA, MAN, MANG, MANGF, MANGFV, MANGFVW,
      MANGFVWE, and MANGFVWEN

<400> SEQUENCE: 2

Xaa Thr Phe Leu Lys Cys Xaa
1               5
```

```
<210> SEQ ID NO 3
<211> LENGTH: 7
<212> TYPE: PRT
<213> ORGANISM: Artificial
<220> FEATURE:
<223> OTHER INFORMATION: synthetic peptide

<400> SEQUENCE: 3

Leu Gly Thr Phe Leu Lys Cys
1               5

<210> SEQ ID NO 4
<211> LENGTH: 11
<212> TYPE: PRT
<213> ORGANISM: Artificial
<220> FEATURE:
<223> OTHER INFORMATION: synthetic peptide

<400> SEQUENCE: 4

His Tyr Leu Gly Thr Phe Leu Lys Cys Met Ala
1               5                   10

<210> SEQ ID NO 5
<211> LENGTH: 9
<212> TYPE: PRT
<213> ORGANISM: Artificial
<220> FEATURE:
<223> OTHER INFORMATION: synthetic peptide

<400> SEQUENCE: 5

Leu Gly Thr Phe Leu Lys Cys Met Ala
1               5

<210> SEQ ID NO 6
<211> LENGTH: 9
<212> TYPE: PRT
<213> ORGANISM: Artificial
<220> FEATURE:
<223> OTHER INFORMATION: synthetic peptide

<400> SEQUENCE: 6

His Tyr Leu Gly Thr Phe Leu Lys Cys
1               5

<210> SEQ ID NO 7
<211> LENGTH: 11
<212> TYPE: PRT
<213> ORGANISM: Artificial
<220> FEATURE:
<223> OTHER INFORMATION: synthetic peptide

<400> SEQUENCE: 7

Gly Thr Phe Leu Lys Cys Met Ala Asn Gly Phe
1               5                   10

<210> SEQ ID NO 8
<211> LENGTH: 11
<212> TYPE: PRT
<213> ORGANISM: Artificial
<220> FEATURE:
<223> OTHER INFORMATION: synthetic peptide

<400> SEQUENCE: 8

Thr Phe Leu Lys Cys Met Ala Asn Gly Phe Val
1               5                   10

<210> SEQ ID NO 9
```

```
<211> LENGTH: 18
<212> TYPE: PRT
<213> ORGANISM: Artificial
<220> FEATURE:
<223> OTHER INFORMATION: synthetic peptide

<400> SEQUENCE: 9

His Tyr Leu Gly Thr Phe Leu Lys Cys Met Ala Asn Gly Phe Val Trp
1               5                   10                  15

Glu Asn

<210> SEQ ID NO 10
<211> LENGTH: 7
<212> TYPE: PRT
<213> ORGANISM: Artificial
<220> FEATURE:
<223> OTHER INFORMATION: synthetic peptide

<400> SEQUENCE: 10

Cys Lys Leu Phe Thr Gly Leu
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Leu Phe Thr Lys Cys
1               5

<210> SEQ ID NO 12
<211> LENGTH: 5
<212> TYPE: PRT
<213> ORGANISM: Artificial
<220> FEATURE:
<223> OTHER INFORMATION: synthetic peptide

<400> SEQUENCE: 12

Cys Lys Thr Phe Leu
1               5

<210> SEQ ID NO 13
<211> LENGTH: 7
<212> TYPE: PRT
<213> ORGANISM: Artificial
<220> FEATURE:
<223> OTHER INFORMATION: synthetic peptide

<400> SEQUENCE: 13

His Thr Leu Met Arg Asn Leu
1               5

<210> SEQ ID NO 14
<211> LENGTH: 7
<212> TYPE: PRT
<213> ORGANISM: Artificial
<220> FEATURE:
<223> OTHER INFORMATION: synthetic peptide

<400> SEQUENCE: 14

Leu Asn Arg Met Leu Thr His
1               5
```

```
<210> SEQ ID NO 15
<211> LENGTH: 7
<212> TYPE: PRT
<213> ORGANISM: Artificial
<220> FEATURE:
<223> OTHER INFORMATION: synthetic peptide

<400> SEQUENCE: 15

Leu Asn Thr Phe Gln Glu Phe
1               5

<210> SEQ ID NO 16
<211> LENGTH: 7
<212> TYPE: PRT
<213> ORGANISM: Artificial
<220> FEATURE:
<223> OTHER INFORMATION: synthetic peptide

<400> SEQUENCE: 16

Phe Glu Gln Phe Thr Asn Leu
1               5

<210> SEQ ID NO 17
<211> LENGTH: 4
<212> TYPE: PRT
<213> ORGANISM: Artificial Sequence
<220> FEATURE:
<223> OTHER INFORMATION: synthetic peptide

<400> SEQUENCE: 17

Thr Phe Leu Lys
1

<210> SEQ ID NO 18
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: "Xaa in position 1" is absent, is glycine or
      represents an aminoacid sequence selected from the group
      consisting of AG, LG, YLG and HYLG
<220> FEATURE:
<221> NAME/KEY: MISC_FEATURE
<222> LOCATION: (6)..(6)
<223> OTHER INFORMATION: "Xaa in position 6" independently is absent or
      is alanine

<400> SEQUENCE: 18

Xaa Thr Phe Leu Lys Xaa
1               5

<210> SEQ ID NO 19
<211> LENGTH: 6
<212> TYPE: PRT
<213> ORGANISM: Artificial Sequence
<220> FEATURE:
<223> OTHER INFORMATION: synthetic peptide

<400> SEQUENCE: 19

Leu Gly Thr Phe Leu Lys
1               5

<210> SEQ ID NO 20
<211> LENGTH: 7
<212> TYPE: PRT
```

```
<213> ORGANISM: Artificial Sequence
<220> FEATURE:
<223> OTHER INFORMATION: synthetic peptide

<400> SEQUENCE: 20

Ala Gly Thr Phe Leu Lys Cys
1               5

<210> SEQ ID NO 21
<211> LENGTH: 7
<212> TYPE: PRT
<213> ORGANISM: Artificial Sequence
<220> FEATURE:
<223> OTHER INFORMATION: synthetic peptide

<400> SEQUENCE: 21

Leu Gly Thr Phe Leu Lys Ala
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic peptide

<400> SEQUENCE: 22

Gly Thr Phe Leu Lys
1               5

<210> SEQ ID NO 23
<211> LENGTH: 7
<212> TYPE: PRT
<213> ORGANISM: Artificial Sequence
<220> FEATURE:
<223> OTHER INFORMATION: synthetic peptide

<400> SEQUENCE: 23

Ala Gly Thr Phe Leu Lys Ala
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic peptide

<400> SEQUENCE: 24

Met Ala Asn Gly
1

<210> SEQ ID NO 25
<211> LENGTH: 5
<212> TYPE: PRT
<213> ORGANISM: Artificial Sequence
<220> FEATURE:
<223> OTHER INFORMATION: synthetic peptide

<400> SEQUENCE: 25

Met Ala Asn Gly Phe
1               5

<210> SEQ ID NO 26
<211> LENGTH: 6
<212> TYPE: PRT
<213> ORGANISM: Artificial Sequence
```

```
<220> FEATURE:
<223> OTHER INFORMATION: synthetic peptide

<400> SEQUENCE: 26

Met Ala Asn Gly Phe Val
1               5

<210> SEQ ID NO 27
<211> LENGTH: 7
<212> TYPE: PRT
<213> ORGANISM: Artificial Sequence
<220> FEATURE:
<223> OTHER INFORMATION: synthetic peptide

<400> SEQUENCE: 27

Met Ala Asn Gly Phe Val Trp
1               5

<210> SEQ ID NO 28
<211> LENGTH: 8
<212> TYPE: PRT
<213> ORGANISM: Artificial Sequence
<220> FEATURE:
<223> OTHER INFORMATION: synthetic peptide

<400> SEQUENCE: 28

Met Ala Asn Gly Phe Val Trp Glu
1               5

<210> SEQ ID NO 29
<211> LENGTH: 9
<212> TYPE: PRT
<213> ORGANISM: Artificial Sequence
<220> FEATURE:
<223> OTHER INFORMATION: synthetic peptide

<400> SEQUENCE: 29

Met Ala Asn Gly Phe Val Trp Glu Asn
1               5

<210> SEQ ID NO 30
<211> LENGTH: 4
<212> TYPE: PRT
<213> ORGANISM: Artificial Sequence
<220> FEATURE:
<223> OTHER INFORMATION: synthetic peptide

<400> SEQUENCE: 30

His Tyr Leu Gly
1
```